United States Patent [19]

Fuisz

[11] Patent Number: 5,028,632

[45] Date of Patent: Jul. 2, 1991

[54] TASTE MASKED MEDICATED PHARMACEUTICAL

[75] Inventor: Richard C. Fuisz, Washington, D.C.

[73] Assignee: Fuisz Pharmaceutical Ltd., Washington, D.C.

[21] Appl. No.: 392,427

[22] Filed: Aug. 10, 1989

Related U.S. Application Data

[63] Continuation-in-part of Ser. No. 325,643, Mar. 20, 1989, which is a continuation-in-part of Ser. No. 283,742, Dec. 13, 1988, which is a continuation-in-part of Ser. No. 169,838, Mar. 18, 1988, Pat. No. 4,855,326, which is a continuation-in-part of Ser. No. 40,371, Apr. 20, 1987, abandoned, said Ser. No. 325,643, is a continuation-in-part of Ser. No. 169,838, , and Ser. No. 169,914, Mar. 18, 1988, Pat. No. 4,873,085, which is a continuation-in-part of Ser. No. 40,371.

[51] Int. Cl.$^5$ .......................... A61K 9/16; A61K 9/20; A61K 9/68; A61K 9/70

[52] U.S. Cl. .................................. 514/772; 514/777; 514/781; 424/410; 424/439; 424/440; 424/443; 426/658; 426/517

[58] Field of Search ............... 514/772, 777, 781, 165; 424/400, 439, 440, 443, 410; 425/9; 426/658, 660, 517; 206/569

[56] References Cited

U.S. PATENT DOCUMENTS 4,855,326  8/1989  Fuisz ................................... 514/777
4,873,085  10/1989  Fuisz ................................... 424/400

*Primary Examiner*—Nathan M. Nutter
*Attorney, Agent, or Firm*—Brooks Haidt Haffner & Delahunty

[57] ABSTRACT

The addition of an extremely small quantity of an anesthetizing agent such as phenol to a medicament dosed saccharide floss serves to numb the taste buds sufficiently that undesirable taste stimulation by the medicament is inhibited.

9 Claims, No Drawings

TASTE MASKED MEDICATED PHARMACEUTICAL

BACKGROUND OF THE INVENTION

This application is a continuation-in-part of application Ser. No. 07/325,643,; Mar, 20, 1989, which is a continuation-in-part of application Ser. No. 07/283,742, filed Dec. 13, 1988, pending a continuation-in-part of application Ser. No. 07/169,838, filed Mar. 18, 1988,now U.S. Pat. No. 4,855,326 which is a continuation-in-part of application Ser. No. 07/040,371, filed Apr. 20, 1987 now abandoned. Application Serial No. 07/325,643 is also a continuation-in-part of said application Ser. No. 07/169,838 now U.S. Pat. No. 4,855,326 and of application Ser. No. 07/169,914, filed Mar. 18, 1988, now U.S. Pat. No. 4,873,085 which is another continuation-in-part of application Serial No. 07/040,371 now abandoned.

In the prior applications preceeding Ser. No. 07/283,742, various substances having pharmacological properties were combined with a sugar and spun into fibers to produce a readily water-soluble product. The various examples enumerated in those applications involved the use of water soluble medicaments and were directed to enhancing the solubility rate of the different substances. It was discovered also that spinning a substance with a sugar can alter the medium in which a particular substance can either dissolve or become dispersed, the latter while forming a colloid or colloidal-like dispersion. When the spun sugar products described in the applications are added to water, the product disperses autogenously throughout the water and remains dispersed. In most instances one observes a general cloudiness associated with a colloidal suspension. But this is not always the case. Several other novel phenomena have been observed also.

The disclosure in application Ser. No. 07/283,742 deals with oleaginous substances such as vegetable oil, baby oil, olive oil, margarine, lanolin, cocoa butter and the like, and how their lack of affinity for water is altered by mixing the oleaginous substance with sugar and melt spinning the mixture in a cotton candy spinning machine or the equivalent. As so modified the products disperse autogenously in water forming a colloidal or colloidal-like dispersion.

In application Ser. No. 07/325,643 it is explained that a spun product from a combination of a saccharide and a hydrophobic ingredient is hydrophillic with low concentrations of such ingredient but becomes increasingly hydrophobic as the concentration of the hydrophobic ingredient is increased, although the end product nevertheless acts hydrophilically when the water temperature is elevated. Larger ratios of hydrophobic substance-to-saccharide yields a spun fibrous product that has increased stability. Similar stabilization can be attained by adding either beeswax or a petrolatum to the saccharide either in the presence of or absence of a separate active ingredient. Control with beeswax can also provide a time release tablet or the like when swallowed.

Examples set forth in said -643 application demonstrate the ability of controlling the floss to mask the taste of a distasteful or unpalatable medicament or the like. Generally, as explained therein, the medicament or active ingredient is not absorbed as rapidly in the mouth as the saccharide. By adding a suitable quantity of beeswax, the release and absorbtion of the saccharide can be slowed to match that of the active ingredient whereby any objectionable taste is successfully masked. Thus, in Example VIII beeswax granules were mixed with sucrose in the ratio of 1:16, and in Example IX the ratio was increased to 1:12. In Example XV where MAALOX antacid suspension, an oral suspension of Magnesia and Alumina, was the medicament, ¼ tsp. ground beeswax USP was blended with 1:6 parts MAALOX to sucrose. The resulting floss when placed as a wad on the tongue, sat on the tongue for about 2 seconds and then was gone within an additional 3 seconds. No aftertaste of the MAALOX antacid could be detected.

Subsequent to filing the -643 application it was determined that by increasing the ratio of beeswax to sucrose over that employed in Example XV of that application, and reducing the ratio of sucrose to MAALOX below that employed in Example XIV of that aplication, it was still possible to mask the taste of MAALOX. However, with more distasteful ingredients such as aspirin it has been found that satisfactory taste masking can not be obtained by merely delaying the dispersal of sucrose.

SUMMARY OF THE PRESENT INVENTION

It is, therefore, an object of the present invention to provide a floss type oral dosage unit that includes a taste masking substance other than the saccharide.

Another object of the invention is to provide a dosage unit containing an effective amount of an ingredient that functions to inhibit undesirable taste stimulation by an unpalatable or distasteful medicament.

Other objects will occur to those skilled in the subject art after reading the present disclosure.

In accordance with one aspect of the present invention there is provided a pharmaceutic dosage unit comprising compacted spun fibers of a spinnable, readily water-soluble material, an effective amount of a medicament, and an effective amount of an ingredient other than said medicament and said material which ingredient, when the dosage unit is taken orally, functions to inhibit undesirable taste stimulation by said medicament.

The invention will be better understood after reading the following detailed description of the presently preferred embodiments thereof.

DETAILED DESCRIPTION OF THE PRESENTLY PREFERRED EMBODIMENTS

Co-pending application Ser. No. 07/169,838 describes methods for combining a medicament with any one or more of the water soluble melt spinnable sugars and spinning the combination to produce a readily soluble floss form of the medicament. The disclosure of such application is incorporated herein by reference.

Co-pending application Ser. No. 07/283,742 discloses that any oleaginous substance that can be mixed with a melt-spinnable sugar, when spun in a cotton candy spinning machine, produces a product which, when added to water or has water added to it, forms, virtually autogenously, a uniform dispersion having all the appearances of a colloidal dispersion. The disclosure of such application is incorporated herein by reference.

Co-pending application Ser. No. 07/325,643 discloses that if the ratio of oleaginous material to sugar (saccharide) exceeds a certain value, the precise crossover point being a function of the particular oleaginous material and sugar, the floss product will no longer disperse rapidly in water at normal room temperature. However, rapid dispersal as an apparent colloidal system does take place at elevated water temperatures. Similar results can be obtained by admixing with the sugar, with or without other ingredients, suitable quantities of certain semi-solid substances that individually are practically insoluble in water, such as beeswax or petrolatum. In general, the fibrous products produced by the examples set forth in that application give the appearance when added to water at normal room temperature of being hydrophobic. Compacted quantities of the fibrous product actually float on the surface of the water. But as soon as the water temperature is raised above some critical level for the particular fiber product, the fibrous product disperses rapidly throughout the body of water forming what appears to be a colloidal dispersion. The present invention can best be described and understood from a consideration of certain examples.

For the following examples the floss spinning machine used was: Econo floss Model 3017 manufactured by Gold Medal Products Co. of Cincinnati, Ohio. Unless otherwise stated, reference to sucrose in the examples is to "Gold Medal" flossugar, lime flavor. Unless otherwise indicated, the temperature of the grid in the spinning machine was about 180° F. (82.2° C.) while the operating speed was about 3800 R.P.M.

EXAMPLE I

¼ tsp. of white beeswax by Spectrum of Gardena, California was placed in a "Braun" chopper having a metal bowl and blades with clear acrylic top. To this was added 1 "Chlorseptic" lozenge by Norwich Eaton Pharmaceuticals. Each lozenge contains as the active ingredients 32.5 mg phenol and sodium phenolate, with inactive ingredients comprising coloring agent, corn syrup, flavor and sucrose. The chopper was operated for about 1 minute until materials were blended into fine powder. The powder was transferred to a mixing vessel to which was added 3 tsp. aspirin USP from Valley Biomedical of Winchester, Virginia, 1/5 tsp. "Crisco" vegetable oil for binding, and ½ cup (24 tsps.) lime flossugar. The ingredients were mixed thoroughly with a spoon for about 4 minutes, and the resulting mixture spun using the floss spinning machine. A nice floss resulted. When a sample of the floss was added to water at room temperature, the floss was observed to float. However, when added to water at 180° F. the floss dispersed immediately while a quantity of telltale white material appeared at the surface. It was concluded that the white material was the aspirin content.

EXAMPLE II

The procedure set forth in Example I was repeated but omitting the "chlorseptic" lozenge. A nice floss resulted.

Having produced the two quantities of floss, one with a phenol content and one without, a quantity of the floss produced in Example II, about the size of a quarter dollar and about ¼" thick, was placed on the tongue of the experimenter. It dispersed in about 4 to 5 seconds leaving a bitter aftertaste characteristic of aspirin.

About 1 hour later, having cleared the palate, the experimenter repeated the test this time using a wad, the same size, of the floss produced in Example I. Again, it took about 4 to 5 seconds to disperse on the tongue. But this time the phenol content apparently numbed slightly the taste buds such that absolutely no aspirin taste could be detected either during the dispersion or by way of aftertaste.

The ratio of the "chlorseptic" lozenge to the aspirin medicament in Example I is believed to be about 1:9. The actual phenol content is less than that relative to the medicament and has been estimated as in the ratio of about 1:40. Moreover, the test described in Example II revealed that the beeswax plus sucrose content by itself was ineffective to cause the sucrose content to mask the taste of the aspirin. However, the small quantity of phenol in the ratio of 1 part phenol to 40 parts aspirin to 320 parts sucrose was completely effective.

Having described the present invention with reference to the presently preferred embodiment, it should be apparent to those skilled in the subject art that various changes in materials and in the process steps can be adopted without departing from the true spirit of the invention as defined in the appended claims.

What is claimed is:

1. A pharmaceutic dosage unit comprising compacted spun fibers of a spinnable, readily water-soluble material, an effective amount of a medicament, and an effective amount of phenol other than said medicament and said material which when the dosage unit is taken orally, functions to inhibit undesirable taste stimulation by said medicament.

2. A pharmaceutic dosage unit according to claim 1, wherein said material is a sugar or a cellulosic material.

3. A pharmaceutic dosage unit according to claim 2, wherein said material is a sugar selected from the group consisting of maltose, fructose, sorbitol, dextrose, mannitol, sucrose, lactose, and combinations thereof.

4. A pharmaceutic dosage unit according to claim 3, wherein said medicament comprises aspirin.

5. A pharmaceutic dosage unit according to claim 1, wherein said medicament comprises aspirin.

6. A pharmaceutic dosage unit according to claim 2, wherein said medicament comprises aspirin.

7. A pharmaceutic dosage unit according to claim 1, wherein said phenol effective amount is within the range capable of numbing without appreciably anesthetizing the taste buds within the oral cavity.

8. A pharmaceutic dosage unit according to claim 7, wherein the ratio of said phenol to said medicament to said material is on the order of 1:40:320.

9. A product for consumption by introduction through the oral cavity where at least one of the ingredients of the product is noticeably unpalatable if introduced alone, said product comprising compacted spun fibers of a spinnable, readily water-soluble palatable material, a quantity of unpalatable ingredient, and an effective quantity of phenol.

* * * * *

UNITED STATES PATENT AND TRADEMARK OFFICE
CERTIFICATE OF CORRECTION

PATENT NO. : 5,028,632
DATED : July 2, 1991
INVENTOR(S) : Richard C. Fuisz It is certified that error appears in the above-identified patent and that said Letters Patent is hereby corrected as shown below:

Column 1, line 7, the text "07/325,643,; Mar, 20," should read --07/325,643, filed Mar. 20,--; line 9, "pending" should be deleted and replaced by --in turn--.

Column 2, lines 5, 6, 8, 12, 16, 18 (each occurrence) "MAALOX" should read --"MAALOX"--.

Column 4, lines 29 and 30, "other than said medicament and said material" should be deleted; line 30, after "which" should be inserted a comma (,).

Signed and Sealed this

Twentieth Day of October, 1992

*Attest:*

DOUGLAS B. COMER

*Attesting Officer*   *Acting Commissioner of Patents and Trademarks*